US008759396B2

(12) United States Patent
Wulf et al.

(10) Patent No.: US 8,759,396 B2
(45) Date of Patent: Jun. 24, 2014

(54) USE OF AMINOLEVULINIC ACID AND DERIVATIVES THEREOF

(75) Inventors: Hans Christian Wulf, Espergerde (DK); Aslak Godal, Oslo (NO); Jo Klaveness, Oslo (NO)

(73) Assignee: Photocure ASA, Oslo (NO)

( * ) Notice: Subject to any disclaimer, the term of this patent is extended or adjusted under 35 U.S.C. 154(b) by 757 days.

(21) Appl. No.: 12/523,048

(22) PCT Filed: Jan. 11, 2008

(86) PCT No.: PCT/GB2008/000086
§ 371 (c)(1),
(2), (4) Date: Jan. 12, 2010

(87) PCT Pub. No.: WO2008/084241
PCT Pub. Date: Jul. 17, 2008

(65) Prior Publication Data
US 2010/0137439 A1    Jun. 3, 2010

(30) Foreign Application Priority Data

Jan. 11, 2007 (GB) .................................. 0700580.4

(51) Int. Cl.
*A01N 37/12* (2006.01)
*A61N 1/30* (2006.01)

(52) U.S. Cl.
USPC ............................................ 514/561; 604/20

(58) Field of Classification Search
USPC ........ 514/94, 95, 100, 254.11, 337, 359, 444, 514/469, 561; 544/376; 546/284.1; 548/119; 604/20
See application file for complete search history.

(56) References Cited

U.S. PATENT DOCUMENTS

| | | | |
|---|---|---|---|
| 5,079,262 A | 1/1992 | Kennedy et al. | |
| 5,211,938 A | 5/1993 | Kennedy et al. | |
| 5,234,940 A | 8/1993 | Kennedy et al. | |
| 5,422,093 A | 6/1995 | Kennedy et al. | |
| 6,034,267 A | 3/2000 | Gierskcky et al. | |
| 6,723,750 B2* | 4/2004 | Voet ............................. | 514/568 |
| 6,897,238 B2 | 5/2005 | Anderson et al. | |
| 2004/0048842 A1 | 3/2004 | McMillan | |
| 2005/0031541 A1* | 2/2005 | Gierskcky et al. ............. | 424/9.6 |
| 2005/0209330 A1 | 9/2005 | Kreindel | |
| 2006/0258629 A1 | 11/2006 | Freeman | |

FOREIGN PATENT DOCUMENTS

| | | |
|---|---|---|
| WO | WO 91/01727 | 2/1991 |
| WO | WO 96/28412 | 9/1996 |
| WO | WO 98/30242 | 7/1998 |
| WO | 0071089 A1 | 11/2000 |
| WO | WO 02/10120 | 2/2002 |
| WO | WO 02/13788 | 2/2002 |
| WO | 03086460 A2 | 10/2002 |
| WO | WO 03/077911 | 9/2003 |
| WO | WO 2005/092838 | 10/2005 |
| WO | WO 2006/051269 | 5/2006 |

OTHER PUBLICATIONS

Beacham (Am. Fam Physician (1992) 46(1) Abstract only.*
Touchin et al (Lasers in Surgery and Medicine 33:296-310 (2003)).*
Madsen Proceedings of SPIE vol. 4612 (2002).*
J.C. Kennedy et al: J. Clin, Laser Med. Surg. (1996) 14: 289-304; Photodynamic Therapy (PDT) and Photodiagnosis (PD) Using Endogenous Photosensitization Induced by 5-Aminolevulinic Acid (ALA): Mechanisms and Clinical Results.
Babilas, Philipp, et al., "Photodynamic therapy in dermatology—an update", Photodermatol. Photoimmunol. Photomed. 2005, vol. 21, pp. 142-149.
Peng, Q. et al, "5-Aminolevulinic Acid-Based Photodynamic Therapy", Cancer (1997) vol. 79:12, pp. 2282-2308.
Sharfaei et al., "Weekly topical application of methyl aminolevulinate followed by light exposure delays the appearance of UV-induced skin tumours in mice," Archives of Dermatological Research, Jul. 2002, vol. 294, No. 5, Jul. 2002, pp. 237-242.
Moan et al., Influence of light exposure on the kinetics of protoporphyrin IX formation in normal skin of hairless mice after application of 5-aminolevulinic acid methyl ester, The Journal of Investigative Dermatology, Nov. 2005, vol. 125, No. 5, Nov. 2005, pp. 1039-1094.
Juzeniene et al., "Topical application of 5-aminolevulinic acid and its methylester, hexylester and octylester derivatives: considerations for dosimetry in mouse skin model," Photochemistry and Photobiology, Sep. 2002, vol. 76, No. 3, Sep. 2002, pp. 329-334.
Itch et al., "Photodynamic Therapy for Acne Vulgaris with Topical 5-Aminolevulinic Acid," Archives of Dermatology, XX, vol. 136, No. 9, Sep. 1, 2000, pp. 1093-1095.
Pollok et al., "Topical aminolaevulinic acid-photodynamic therapy for the treatment of acne vulgaris: a study of clinical efficacy and mechanism of action," The British Journal of Dermatology, Sep. 2004, vol. 151, No. 3, Sep. 2004, pp. 616-622.

(Continued)

*Primary Examiner* — Shirley V Gembeh
(74) *Attorney, Agent, or Firm* — Kenyon and Kenyon LLP

(57) ABSTRACT

The invention provides the use of a photosensitizer which is 5-aminolevulinic acid (5-ALA) or a derivative (e.g. an ester) of 5-ALA, or a pharmaceutically acceptable salt thereof, in the manufacture of a composition for use in methods of photodynamic therapy (PDT) on an animal, wherein said PDT comprises: (a) administering to said animal a composition comprising said photosensitizer; and (b) photoactivating said photosensitizer, and wherein side-effects (e.g. pain and/or erythema) of said PDT are prevented or reduced by use of one or more of (i)-(iv): (i) said composition comprises said photosensitizer in a concentration of less than 10% wt (e.g. 0.5 to 8% wt), (ii) said composition is administered for less than 2 hours (e.g. 30 minutes to 90 minutes) prior to said photoactivation, (iii) said photoactivation is carried out with a light source having a fluence rate of less than 50 mW/cm$^2$ (e.g. 5 to 40 mW/cm$^2$), (iv) said photoactivation is carried out with sunlight. Preferably, side-effects of PDT are prevented or reduced by using (iii) or (iv) in combination with (i) and/or (ii).

16 Claims, No Drawings

(56) References Cited

OTHER PUBLICATIONS

Wiegell et al., "Pain associated with photodynamic therapy using 5-aminolevulinic acid of 5-aminolevulinic acid methylester on tape-stripped normal skin," Archives of Dermatology, 139(9), pp. 1173-1177, 2003.

Tarstedt et al., "A randomized multicenter study to compare actinic keratosis of the face of the face and scalp." Acta Dermatovenereologica 2005; vol. 85, No. 5, pp. 424-428.

Horfelt et al., "Topical methyl aminolaevulinate photodynamic therapy for treatment of facial acne vulgaris: results of a randomized, controlled study." The British Journal of Dermatology Sep. 2006, vol. 155, No. 3, Sep. 2006. pp. 608-613.

Cases et al., "Photosensitization and mechanism of cytotoxicity induced by the use of ALA derivatives in photodynamic therapy." British Journal of Cancer, 85(2), 279-284, 2001.

Woodford et al., J. Toxicol. Cut & Ocular Toxicology, 1986, 5: 167-177.

Stoughton et al., Drug Dpv. Ind. Pharm. 183, 9: 725-744, 1983.

* cited by examiner

USE OF AMINOLEVULINIC ACID AND DERIVATIVES THEREOF

RELATED APPLICATIONS

This is the national phase of PCT Application No. PCT/GB2008/000086 filed Jan. 11, 2008, which claims priority to British Patent Application No. 0700580.4, the entire contents of which are incorporated herein.

This invention relates to photodynamic therapy (PDT), and in particular to the use of 5-aminolevulinic acid (5-ALA) and derivatives of 5-ALA in PDT wherein the side-effects (e.g. pain and/or erythema) of PDT are prevented or reduced.

PDT, or photochemotherapy as it is also known, is a technique for the treatment of various abnormalities or disorders of the skin or other epithelial organs or mucosa, especially cancers or pre-cancerous lesions, as well as certain non-malignant lesions (e.g. skin complaints such as psoriasis, actinic keratoses (AK) and acne). PDT involves the application of photosensitizing (photochemotherapeutic) agents to the affected area of the body, followed by exposure to photo-activating light in order to activate the photosensitizing agents and convert them into cytotoxic form, whereby the affected cells are killed or their proliferative potential diminished.

A range of photosensitizing agents are known, including the psoralens, the porphyrins (e.g. Photofrin®), the chlorins and the phthalocyanins. Amongst the most clinically useful photosensitizing agents known in the art, however, are 5-aminolevulinic acid and its derivatives, for example esters such as 5-ALA esters.

Although PDT with 5-ALA and 5-ALA derivatives is clinically useful in the treatment of a wide range of diseases, a major draw back of such treatment is the concomitant side-effects, particularly at the treatment site. These often include pain, erythema, swelling, edema, burning, itching, exfoliation, hyperpigmentation and prolonged irritation and hypersensitivity after treatment. Such side-effects are particularly undesirable when the treatment site is the face, scalp or neck. This is frequently the case when the PDT is for the treatment of lesions (e.g. acne, basal cell carcinoma, actinic keratosis, squamous cell carcinoma).

The occurrence of such side effects is recognised in WO2006/051269 which discloses use of 5-ALA esters in PDT for the treatment of acne. WO2006/051269 describes a study wherein a cream comprising 16% wt methyl ALA ester is applied to the faces of subjects for 3 hours followed by exposure of the subjects' faces to non-coherent red light (light dose 37 Jcm$^{-2}$). The treatment was then repeated 2 weeks later. Although the results confirmed that PDT with methyl ALA ester is effective in the treatment of acne, the subjects also indicated that the treatment caused some pain.

WO02/13788 discloses a similar study on use of ALA acid in PDT for the treatment of acne. In this case 20% ALA acid was applied to the backs of the subjects for 3 hours and then the subjects were exposed to 150 J/cm$^2$ broad band light. Again the results confirmed that PDT with ALA is effective for the treatment of acne, but the subjects also reported a plethora of undesirable side effects. For example, WO02/13788 reports that erythema, hyperpigmentation and exfoliation were often seen after PDT treatment and states that in some cases a subsequent treatment even had to be postponed. Reports of pain, burning and itching during and after treatment were also common.

WO02/13788 describes the above-described treatment regime as a "high dose, high energy" regime and it is said to provide a permanent improvement to acne. WO02/13788 additionally discloses a "low dose, low energy" regime that is said to be designed to provide relief from acne. In this treatment 0.1 to 10% wt ALA acid is applied, and after waiting for the ALA acid to penetrate the skin, is followed by irradiation with a light dose of 1 to 20 J/cm$^2$. WO02/13788 suggests that this regime be used in occasional multiple treatments to alleviate acne and be repeated as necessary to maintain diminishment thereof. Although it is recognised that use of such a regime may be pain free, the implication in WO02/13788 is that the therapeutic effect of this treatment regime is less than the high dose, high energy regime it describes and exemplifies.

A need still therefore exists for alternative PDT methods that are free from undesirable side effects (e.g. pain) but which have high therapeutic efficacy.

It has now surprisingly been found that substantially pain free (e.g. pain free), therapeutically acceptable, PDT can be achieved by modifying the photosensitiser-composition used in the PDT and/or altering the PDT procedure.

Thus viewed from a first aspect the invention provides the use of a photosensitiser which is 5-aminolevulinic acid (5-ALA) or a derivative (e.g. an ester) of 5-ALA, or a pharmaceutically acceptable salt thereof, in the manufacture of a composition for use in photodynamic therapy (PDT) on an animal, wherein said PDT comprises:
  (a) administering to said animal a composition comprising said photosensitiser; and
  (b) photoactivating said photosensitiser,
and side-effects (e.g. pain and/or erythema) of said PDT are prevented or reduced by use of one or more of (i)-(iv):
  (i) said composition comprises said photosensitiser in a concentration of less than 10% wt (e.g. 0.5 to 8% wt),
  (ii) said composition is administered for less than 2 hours (e.g. 30 minutes to 90 minutes) prior to said photoactivation,
  (iii) said photoactivation is carried out with a light source having a fluence rate of less than 50 mW/cm$^2$ (e.g. 5 to 40 mW/cm$^2$),
  (iv) said photoactivation is carried out with sunlight.

Viewed from a further aspect, the invention provides a method of preventing or reducing side-effects (e.g. pain and/or erythema) of photodynamic therapy (PDT) in an animal, wherein said PDT comprises:
  (a) administering to said animal a composition comprising a photosensitiser as hereinbefore defined; and
  (b) photoactivating said photosensitiser,
and side-effects of said PDT are prevented or reduced by use of one or more of (i)-(iv):
  (i) said composition comprises said photosensitiser in a concentration of less than 10% wt (e.g. 0.5 to 8% wt),
  (ii) said composition is administered for less than 2 hours (e.g. 30 minutes to 90 minutes) prior to said photoactivation,
  (iii) said photoactivation is carried out with a light source having a fluence rate of less than 50 mW/cm$^2$ (e.g. 5 to 40 mW/cm$^2$),
  (iv) said photoactivation is carried out with sunlight.

In a particularly preferred aspect of the invention, side-effects of PDT are prevented or reduced by use of (iii) or (iv) in combination with one or both of (i) and (ii).

In preferred uses and methods of the invention, the PDT has substantially the same therapeutic effect as the corresponding standard PDT treatment.

By the term "animal" is meant herein any human or non-human being. Preferred animals for treatment in accordance with the invention are humans.

The use of 5-ALA and derivatives of 5-ALA (5-amino-4-oxo-pentanoic acid, otherwise known as 5-aminolevulinic acid) in PDT is well known in the scientific and patent literature (see, for example, J. C. Kennedy et al., J. Clin. Laser Med. Surg. (1996) 14: 289-304, U.S. Pat. No. 5,079,262, U.S. Pat. No. 5,211,938, U.S. Pat. No. 5,234,940, U.S. Pat. No. 5,422,093, U.S. Pat. No. 6,034,267, WO91/01727, WO96/28412, WO2005/092838 and WO2006/051269, the contents of which are incorporated herein by reference). 5-ALA and all such derivatives of 5-ALA, as well as their pharmaceutically acceptable salts, are suitable for the uses and methods herein described.

The 5-ALA derivatives useful in accordance with the invention may be any derivative of 5-ALA capable of forming protoporphyrin IX (PpIX) or any other photosensitiser (e.g. a PpIX derivative) in vivo. Typically, such derivatives will be a precursor of PpIX or of a PpIX derivative (e.g. a PpIX ester) in the biosynthetic pathway for haem and which are therefore capable of inducing an accumulation of PpIX at the site to be treated following administration in vivo. Suitable precursors of PpIX or PpIX derivatives include 5-ALA prodrugs which might be able to form 5-ALA in vivo as an intermediate in the biosynthesis of PpIX or which may be converted (e.g. enzymatically) to porphyrins without forming 5-ALA as an intermediate. 5-ALA esters are among the preferred compounds for use in the methods herein described.

Esters of 5-aminolevulinic acid and N-substituted derivatives thereof are preferred photosensitisers for use in the invention. Those compounds in which the 5-amino group is unsubstituted (i.e. the ALA esters) are particularly preferred. Such compounds are generally known and described in the literature (see, for example, WO96/28412, WO02/10120 and WO2005/092838 to PhotoCure ASA, the contents of which are incorporated herein by reference).

Esters of 5-aminolevulinic acid with substituted or unsubstituted alkanols, i.e. alkyl esters are especially preferred photosensitisers for use in the invention. Examples of such compounds include those of general formula I:

$$R^2_2N\text{---}CH_2COCH_2\text{---}CH_2CO\text{---}OR^1 \qquad (I)$$

(wherein $R^1$ represents a substituted or unsubstituted straight-chained, branched or cyclic alkyl group (e.g. a substituted or unsubstituted straight-chained alkyl group); and each $R^2$ independently represents a hydrogen atom or an optionally substituted alkyl group, e.g. a group $R^1$) and pharmaceutically acceptable salts thereof.

As used herein, the term "alkyl", unless stated otherwise, includes any long or short chain, cyclic, straight-chained or branched aliphatic saturated or unsaturated hydrocarbon group. The unsaturated alkyl groups may be mono- or poly-unsaturated and include both alkenyl and alkynyl groups. Unless stated otherwise, such groups may contain up to 40 atoms. However, alkyl groups containing up to 30, preferably up to 10, particularly preferably up to 8, especially preferably up to 6, e.g. up to 4 carbon atoms are preferred.

The substituted alkyl $R^1$ and $R^2$ groups may be mono or poly-substituted. Suitable substituents may be selected from hydroxy, alkoxy, acyloxy, alkoxycarbonyloxy, amino, aryl, nitro, oxo, fluoro, —$SR_3$, —$NR^3_2$ and —$PR^3_2$ groups, and each alkyl group may be optionally interrupted by one or more —O—, —$NR_3$—, —S— or —$PR_3$— groups, in which $R^3$ is a hydrogen atom or a $C_{1-6}$ alkyl group).

Preferred substituted alkyl $R^1$ groups include those carrying one or more oxo groups, preferably straight-chained $C_{4-12}$ alkyl (e.g. $C_{8-10}$ alkyl) groups substituted by one, two or three (preferably two or three) oxo groups. Examples of such groups include 3,6-dioxa-1-octyl and 3,6,9-trioxa-1-decyl groups.

Particularly preferred for use in the invention are those compounds of formula I in which at least one $R^2$ represents a hydrogen atom. In especially preferred compounds each $R^2$ represents a hydrogen atom.

Compounds of formula I in which $R^1$ represents an unsubstituted alkyl group (preferably $C_{1-8}$ alkyl, e.g. $C_{1-6}$ alkyl) or an alkyl group (e.g. $C_{1-2}$ alkyl, especially $C_1$ alkyl) substituted by a substituent as hereinbefore defined (e.g. by an aryl group such as phenyl or by an alkoxy group such as methoxy) are also preferred.

Unsubstituted alkyl groups which may be used in the invention include both branched and straight-chained hydrocarbon groups. Compounds of formula I in which $R^1$ is a $C_{4-8}$, preferably a $C_{5-8}$, straight chain alkyl group which is branched by one or more $C_{1-6}$ (e.g. $C_{1-2}$ alkyl) groups are preferred. Representative examples of suitable unsubstituted branched alkyl groups include 2-methylpentyl, 4-methylpentyl, 1-ethylbutyl and 3,3-dimethyl-1-butyl. 4-methylpentyl is particularly preferred.

Compounds of formula I in which $R^1$ is a $C_{1-10}$ straight-chained alkyl group are also preferred. Representative examples of suitable unsubstituted alkyl groups include methyl, ethyl, propyl, butyl, pentyl, hexyl and octyl (e.g. n-propyl, n-butyl, n-pentyl, n-hexyl and n-octyl). Hexyl, especially n-hexyl, is a particularly preferred group. Methyl is also particularly preferred.

Also preferred for use in the invention are those compounds of formula I in which $R^1$ represents a $C_{1-2}$ alkyl group (preferably a $C_1$ alkyl group) optionally substituted by an aryl group.

Still further preferred for use in the invention are those compounds of formula I in which $R^1$ represents an alkyl group (e.g. $C_{1-2}$ alkyl, especially $C_1$ alkyl) substituted by an aryl group (e.g. phenyl). Preferred substituted alkyl $R^1$ groups which may be present in compounds of formula I include $C_{1-6}$ alkyl, preferably $C_{1-4}$ alkyl, particularly preferably $C_1$ or $C_2$ alkyl (e.g. $C_1$ alkyl) substituted (preferably terminally substituted) by an optionally substituted aryl group.

By an "aryl group" is meant a group which is aromatic. Preferred aryl groups comprise up to 20 carbon atoms, more preferably up to 12 carbon atoms, for example, 10 or 6 carbon atoms.

Aryl groups which may be present in the compounds of the invention may be heteroaromatic (e.g. 5-7 membered heteroaromatics) but are preferably non-heteroaromatic. By "non-heteroaromatic" is meant an aryl group having an aromatic system comprising electrons originating solely from carbon atoms. Preferred aryl groups include phenyl and napthyl, especially phenyl. In preferred compounds for use in the invention one or two aryl groups may be present, preferably one.

Aryl groups which may be present in the compounds of the invention may optionally be substituted by one or more (e.g. 1 to 5), more preferably one or two, groups (e.g. one group). Preferably the aryl group is substituted at the meta or para position, most preferably the para position. Suitable substituent groups may include haloalkyl (e.g. trifluoromethyl), alkoxy (i.e. —OR groups wherein R is preferably a $C_{1-6}$ alkyl group), halo (e.g. iodo, bromo, more especially chloro and fluoro), nitro and $C_{1-6}$ alkyl (preferably $C_{1-4}$ alkyl). Preferred $C_{1-6}$ alkyl groups include methyl, isopropyl and t-butyl, particularly methyl. Particularly preferred substituent groups include chloro and nitro. Still more preferably the aryl group is unsubstituted.

In a further preferred aspect the invention provides the use of a photosensitiser which is a compound of formula I wherein $R^1$ represents an aryl substituted $C_{1-4}$ alkyl group (preferably $C_{1-2}$, e.g. $C_1$), preferably wherein said aryl group comprises up to 20 carbon atoms (e.g. up to 12 carbon atoms, especially 6 carbon atoms) and is itself optionally substituted, and each $R^2$ is as hereinbefore defined (e.g. each $R^2$ is hydrogen), or a pharmaceutically acceptable salt thereof in the manufacture of a medicament for use in PDT.

Preferred compounds for use in the invention include methyl ALA ester, ethyl ALA ester, propyl ALA ester, butyl ALA ester, pentyl ALA ester, hexyl ALA ester, octyl ALA ester, 2-methoxyethyl ALA ester, 2-methylpentyl ALA ester, 4-methylpentyl ALA ester, 1-ethylbutyl ALA ester, 3,3-dimethyl-1-butyl ALA ester, benzyl ALA ester, 4-isopropylbenzyl ALA ester, 4-methylbenzyl ALA ester, 2-methylbenzyl ALA ester, 3-methylbenzyl ALA ester, 4-[t-butyl]benzyl ALA ester, 4-[trifluoromethyl]benzyl ALA ester, 4-methoxybenzyl ALA ester, 3,4-[di-chloro]benzyl ALA ester, 4-chlorobenzyl ALA ester, 4-fluorobenzyl ALA ester, 2-fluorobenzyl ALA ester, 3-fluorobenzyl ALA ester, 2,3,4,5,6-pentafluorobenzyl ALA ester, 3-nitrobenzyl ALA ester, 4-nitrobenzyl ALA ester, 2-phenylethyl ALA ester, 4-phenylbutyl ALA ester, 3-pyridinyl-methyl ALA ester, 4-diphenyl-methyl ALA ester and benzyl-5-[(1-acetyloxyethoxy)-carbonyl]amino levulinate.

Still further preferred compounds for use in the invention include methyl ALA ester, ethyl ALA ester, 2-methoxyethyl ALA ester, benzyl ALA ester, 4-isopropylbenzyl ALA ester, 4-methylbenzyl ALA ester, 2-methylbenzyl ALA ester, 3-methylbenzyl ALA ester, 4-[t-butyl]benzyl ALA ester, 4-[trifluoromethyl]benzyl ALA ester, 4-methoxybenzyl ALA ester, 3,4-[di-chloro]benzyl ALA ester, 4-chlorobenzyl ALA ester, 4-fluorobenzyl ALA ester, 2-fluorobenzyl ALA ester, 3-fluorobenzyl ALA ester, 2,3,4,5,6-pentafluorobenzyl ALA ester, 3-nitrobenzyl ALA ester, 4-nitrobenzyl ALA ester, 2-phenylethyl ALA ester, 4-phenylbutyl ALA ester, 3-pyridinyl-methyl ALA ester, 4-diphenyl-methyl ALA ester and benzyl-5-[(1-acetyloxyethoxy)-carbonyl]amino levulinate.

Particularly preferred compounds for use in the invention include methyl ALA ester, hexyl ALA ester and benzyl ALA ester, especially methyl ALA ester.

The compounds for use in the invention may be prepared by any conventional procedure available in the art (e.g. as described in WO02/10120 to PhotoCure ASA). For example, esters of 5-ALA may be prepared by reaction of 5-ALA with the appropriate alcohol in the presence of acid. Alternatively compounds for use in the invention may be available commercially (e.g. from Photocure ASA, Norway).

The compounds for use according to the invention may be in the form of a free amine (e.g. —NH$_2$, —NHR$^2$ or —NR$^2$R$^2$) or preferably in the form of a physiologically acceptable salt. Such salts preferably are acid addition salts with physiologically acceptable organic or inorganic acids. Suitable acids include, for example, hydrochloric, nitric, hydrobromic, phosphoric, sulphuric, sulphonic and sulphonic acid derivatives. Hydroiodic acids may also be suitable. Particularly preferred salts are acid addition salts with hydrochloric acid and sulphonic acid derivatives (e.g. mesylate or tosylate) as described in WO2005/092838 to PhotoCure ASA, the entire contents of which are incorporated herein by reference. Procedures for salt formation are conventional in the art.

In the uses and methods of the invention a single photosensitiser as hereinbefore defined (i.e. 5-ALA or a derivative of 5-ALA) may be used alone in PDT. Alternatively, a combination of two or more; preferably two, photosensitisers may be used wherein at least one of the photosensitisers is selected from 5-ALA and derivatives of 5-ALA, or a pharmaceutically acceptable salt thereof.

Other photosensitisers which may be formulated with 5-ALA or a derivative of 5-ALA (e.g. a 5-ALA ester) or co-administered in accordance with the invention include:

Hematoporphyrin derivative (HpD);

Hematoporphyrins such as Photofrin® (Quadra Logic Technologies Inc., Vancouver, Canada) and Hematoporphyrin IX (HpIX);

Photosan III (Seehof Laboratorium GmbH, Seehof, Wesselburenerkoog, Germany);

Chlorins such as tetra(m-hydroxyphenyl)chlorins (m-THPC) and their bacteriochlorins (Scotia Pharmaceuticals Ltd, Surrey, UK), mono-L-aspartyl chlorin e6 (NPe6) (Nippon Petrochemical Co., CA, USA), chlorin e6 (Porphyrin Products Inc.), benzoporphyrins (Quadra Logic Technologies Inc., Vancouver, Canada) (e.g. benzoporphyrin derivative monoacid ring A, BPD-MA) and purpurines (PDT Pharmaceuticals Inc., CA, USA) (e.g. tin-ethyl etiopurpurin, SnET2);

phthalocyanines (e.g. zinc-(Quadra Logic Technologies Inc., Vancouver, Canada), some aluminium- or silicon phthalocyanines, which may be sulfonated, in particular sulfonated phthalocyanines such as aluminium phthalocyanine disulfonate (AlPcS$_{2a}$) or aluminium phthalocyanine tetra-sulfonate (AlPcS$_4$));

porphycenes;

hypocrellins;

Protoporphyrin IX (PpIX);

Hematoporphyrin di-ethers;

Uroporphyrins;

Coproporphyrins;

Deuteroporphyrin;

Polyhematoporphyrin (PHP), and precursors and derivatives thereof; and antibiotics such as tetracycline (e.g. Topicycline®, Shire).

Preferably the second photosensitiser will be a Hematoporphyrin (e.g. Photofrin®), a chlorin (particularly m-THPC or chlorin e6) or a sulphonated phthalocyanine (particularly aluminium phthalocyanine di-sulfonate or aluminium phthalocyanine tetra-sulfonate).

If a second photosensitiser is used together with 5-ALA or 5-ALA derivatives according to the uses and methods of the present invention, the PDT conditions still preferably ensure that few, if any, side effects of treatment occur. This may be achieved by use of at least one of (i)-(iv) as hereinbefore described and optionally a low dose (e.g. sub-therapeutic dose) of the second photosensitiser.

Thus in a further aspect the invention provides the use of a first photosensitiser which is 5-ALA or a derivative of 5-ALA as hereinbefore defined, or a pharmaceutically acceptable salt thereof, together with a second photosensitiser in the manufacture of a composition for use in PDT as hereinbefore defined.

Furthermore the compounds for use according to the invention may be formulated and/or administered with other active components which are able to increase the photosensitizing effect and thus enhance the PDT. For example, chelating agents may beneficially be included and/or co-administered in order to enhance the accumulation of Pp; the chelation of iron by the chelating agent prevents its incorporation into Pp to form haem by the action of the enzyme ferrochelatase, thereby leading to a build-up of Pp. The photosensitizing effect is thus enhanced.

Suitable chelating agents include aminopolycarboxylic acids, including any of the chelants described in the literature for metal detoxification or for the chelation of paramagnetic metal ions in magnetic resonance imaging contrast agents.

Particular mention may be made of EDTA, CDTA (cyclohexane diamine tetraacetic acid), DTPA and DOTA and well known derivatives/analogues thereof EDTA and DTPA are particularly preferred. To achieve the iron-chelating effect, desferrioxamine and other siderophores may also be used, e.g. in conjunction with aminopolycarboxylic acid chelating agents such as EDTA.

Where present, the chelating agent may conveniently be used at a concentration of 0.05 to 20%, e.g. 0.1 to 10% (w/w).

Penetration enhancers may also have a beneficial effect in enhancing the photosensitizing effect of the compounds for use in the invention. Surface-penetration assisting agents, especially dialkylsuphoxides such as dimethylsulphoxide (DMSO), may therefore also be included in the compositions for use in the invention and/or co-administered. The surface-penetration assisting agent may be any of the skin-penetration assisting agents described in the pharmaceutical literature e.g. chelators (e.g. EDTA), surfactants (e.g. sodium dodecyl sulphate), non-surfactants, bile salts (e.g. sodium deoxycholate) and fatty acids (e.g. oleic acid). Examples of appropriate surface penetrating assisting agents include isopropanol, HPE-101 (available from Hisamitsu), DMSO and other dialkylsulphoxides, in particular n-decylmethyl-sulphoxide (NDMS), dimethylsulphacetamide, dimethylformamide (DMFA), dimethylacetamide, glycols, various pyrrolidone derivatives (Woodford et al., *J. Toxicol. Cut. & Ocular Toxicology*, 1986, 5: 167-177), and Azone® (Stoughton et al., *Drug Dpv. Ind. Pharm.* 1983, 9: 725-744), or mixtures thereof.

The surface penetration agent may conveniently be provided in a concentration range of 0.2 to 50% (w/w), e.g. about 10% (w/w).

The compositions for use in accordance with the invention may additionally include lubricating agents, wetting agents, emulsifying agents, suspending agents, preserving agents, sweetening agents, flavouring agents, adsorption enhancers, e.g. surface penetrating agents as mentioned below, and the like.

The compounds for use according to the invention may be formulated in any conventional manner with one or more physiologically acceptable carriers or excipients, according to techniques well known in the art. Where appropriate, compounds or compositions for use in the invention are sterilized, e.g. by γ-irradiation, autoclaving or heat sterilization, before or after the addition of a carrier or excipient where that is present, to provide sterile formulations. The compositions of the invention may also be formulated so as to provide quick, sustained or delayed release of the active ingredient after administration to the patient by employing procedures well known in the art. Solubilizing and/or stabilizing agents may, for example, be used, e.g. cyclodextrins (CD) α, β, γ and HP-β cyclodextrin. Compositions may be in any appropriate dosage form, for example as an emulsion or in liposomes, niosomes, microspheres, nanoparticles or the like. The compounds for use in the invention may then be absorbed to, incorporated in or bound to these forms.

The pH in the final composition is preferably in the range 2.5 to 7.4. Slightly acidic pH, for example pH 5-7, is preferred.

Compositions may be administered systemically (e.g. orally or parenterally) or more preferably locally (e.g. by injection or topically) at or near the affected site. The route of administration will depend on the severity, nature and location of the disease to be treated as well as the photosensitiser (or combination of photosensitisers) used. Generally, however, local administration, still more preferably, topical application is preferred. Topical administration to inaccessible sites may be achieved by techniques known in the art, e.g. by the use of catheters or other appropriate drug delivery systems.

Compositions that may be administered systemically include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof.

Compositions that may be administered locally (e.g. topically) include gels, creams, ointments, sprays, lotions, salves, sticks, soaps, powders, pessaries, aerosols, drops, solutions and any of the other conventional pharmaceutical forms in the art. Creams, ointments and gels are especially preferred.

Creams, ointments and gels may be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Particularly preferably the compositions for use in PDT according to the invention will be in the form of a ready-to-use composition such as a cream or as a kit as hereinbefore defined.

The concentration of the 5-ALA compounds described herein in the final compositions for PDT will vary depending on several factors including the chemical nature of the compound, the chemical composition, mode of administration and nature of the disease to be treated. Preferably, however, concentration ranges of less than 20% wt, more preferably less than 10% wt, still more preferably 0.05 to 8% wt, yet more preferably 0.5 to 6% wt, e.g. 1.5 to 4.5% wt or 2 to 4% wt are used. The most preferred concentrations for local (e.g. topical) administration is in the range 2 to 4% wt.

Thus viewed from a yet further aspect the invention provides a pharmaceutical composition comprising a photosensitiser which is 5-ALA or a derivative of 5-ALA as hereinbefore defined and a pharmaceutically acceptable carrier or excipient, wherein the concentration of said photosensitiser is 2 to 8% wt (e.g. 2 to 4.5% wt).

Viewed from a still further aspect the invention provides a pharmaceutical composition comprising a photosensitiser which is 5-ALA or a derivative of 5-ALA as hereinbefore defined and a pharmaceutically acceptable carrier or excipient, wherein the concentration of said photosensitiser is 2 to 8% wt (e.g. 2 to 4.5% wt) for use in therapy (e.g. PDT).

Viewed from a still further aspect the invention provides a product or kit for use in a method of preventing or reducing side-effects (e.g. pain and/or erythema) of photodynamic therapy (PDT) in an animal comprising:

(a) a container containing a composition as hereinbefore defined (e.g. a composition comprising a photosensitiser which is 5-ALA or a derivative of 5-ALA at a concentration of less than 20% wt, e.g. less than 10% wt), and (b) instructions for carrying out said PDT as herein defined.

In particularly preferred products and kits, the composition contained in the first container comprises the composition which itself forms an aspect of the invention (i.e. a composition comprising a photosensitiser which is 5-ALA or a derivative of 5-ALA as hereinbefore defined in a concentration of 2 to 8% wt (e.g. 2 to 4.5 wt %)). Further preferred products and kits comprise a second container containing a second photosensitiser, e.g. as hereinbefore defined.

The instructions present in the products and kits of the invention describe the steps of administering the composition comprising a photosensitiser to an animal and photoactivating the photosensitiser. The instructions also preferably describe at least one of steps (ii), (iii) or (iv) as herein defined.

PDT is carried out by administering to an animal a composition comprising a photosensitiser as hereinbefore defined and photoactivating the photosensitiser. By use of at least one of (i)-(iv) as hereinbefore defined the side effects of PDT are prevented or reduced. By "side effects" is meant herein effects, usually undesirable effects, caused by PDT, other than its desired therapeutic effect. Representative examples of side effects commonly associated with PDT include pain, erythema, swelling, edema, burning, itching, exfoliation, hyperpigmentation and prolonged irritation and hypersensitivity after treatment. The uses and methods of the present invention are particularly useful for preventing or reducing pain and/or erythema, especially pain.

In particularly preferred uses and methods of the invention, the PDT has substantially the same therapeutic effect as the corresponding standard PDT treatment, whilst preventing or reducing the side effects of the standard treatment. By the term "corresponding standard PDT treatment" is meant the PDT treatment carried out with the same photosensitiser (e.g. the same 5-ALA ester) and the same light dose (e.g. 37 $J/cm^2$), but under the following conditions:

(I) the concentration of the photosensitiser is at least 15% wt (e.g. 16% wt), (II) the photosensitiser is administered for at least 3 hours (e.g. 3 hours) prior to photoactivation; and (III) photoactivation is carried out with a light source having a fluence rate of at least 60 $mW/cm^2$, e.g. about 70 $mW/cm^2$.

Particularly preferred uses and methods of the invention provide at least 90%, still more preferably at least 95%, e.g. at least 99% of the therapeutic effect of the corresponding standard PDT treatment.

In preferred uses and methods of the invention, side effects of PDT are prevented or reduced by use of (i) as hereinbefore described, i.e. use of a composition comprising the photosensitiser in a concentration of less than 10% wt (e.g. 0.5 to 8% wt). Particularly preferred compositions comprise photosensitiser in a concentration of 0.05 to 8% wt, still more preferably 0.5 to 6% wt, e.g. 1 to 4.5% wt or 2 to 4% wt.

In further preferred uses and methods of the invention, the composition comprising the photosensitiser(s) as hereinbefore described is administered to the animal and a certain time period is allowed to elapse before the site to be treated is exposed to light to achieve the desired photosensitizing effect. By the term "administered" is meant that the composition is delivered to the animal. This may be achieved, for example, by applying the composition to the skin and allowing it to permeate therethrough. Preferably the composition is administered in a single application. Before light exposure, excess photosensitiser is preferably removed.

The length of time following administration at which light exposure takes place will depend on the nature of the composition, the condition to be treated and the form of administration. It may be, for example, about 3 to 6 hours. In preferred uses and methods of the invention, however, side effects of PDT are prevented or reduced by use of (ii) as hereinbefore defined, i.e. by administering the composition for less than 2 hours prior to photoactivation. Still more preferably the composition is administered for 0 to 90 minutes (e.g. 5 to 90 minutes, preferably 30 to 90 minutes), more preferably 10 to 50 minutes, still more preferably 15 to 45 minutes, e.g. 20 to 40 minutes prior to photoactivation. In a particularly preferred aspect of the invention, light exposure may be effected immediately after administration of the photosensitiser, i.e. the period of administration may be a matter of only minutes (e.g. up to 10 minutes, more preferably up to 5 minutes) or may effectively be zero in the case where administration and photoactivation occur simultaneously.

In the uses and methods of the invention, photoactivation may be achieved using light sources known in the art. Methods for the irradiation of different areas of the body, e.g. by lamps or lasers are well known in the art (see for example Van den Bergh, Chemistry in Britain, May 1986 p. 430-439). The wavelength of light used for irradiation may be selected to achieve a more efficacious photosensitizing effect. The most effective light is light in the wavelength range 300-800 nm, typically 400-700 nm. The irradiation will in general be applied at a dose level of 40 to 200 $Joules/cm^2$, for example at 100 $Joules/cm^2$. A light source having a fluence rate of 60 to 100 $mW/cm^2$ may be used.

In particularly preferred uses and methods of the invention, side effects of PDT are prevented or reduced by use of (iii) as hereinbefore described, i.e. by photoactivating with a light source having a fluence rate of less than 50 $mW/cm^2$. Still more preferably photoactivation is carried out with a light source having a fluence rate of 5 to 40 $mW/cm^2$, still more preferably 10 to 35 $mW/cm^2$, e.g. 15 to 35 $mW/cm^2$.

Still more preferably the irradiation is applied at a dose of 10 to 100 $J/cm^2$, more preferably 20 to 60 $J/cm^2$, e.g. about 37 $Joules/cm^2$. Penetration of light into tissues depends on the wavelength used and is deeper for red light than for blue light. Irradiation is preferably performed for 5 to 30 minutes, preferably for 15 minutes, depending on the light dose and fluence rate. A single irradiation may be used or alternatively a light split dose in which the light dose is delivered in a number of fractions, e.g. a 1 to 10 minutes between irradiations, may be used.

In further preferred uses and methods of the invention, side effects of PDT are prevented or reduced by use of (iv) as hereinbefore defined, i.e. by photoactivating with sunlight. This aspect of the invention includes photoactivation with either natural sunlight or any light source which provides artificial sunlight (i.e. the entire range from UV to IR). Use of natural sunlight as the light source has the advantage that the animal being treated is free to leave the clinical environment where treatment is normally conducted. Furthermore, as the intensity of sunlight (whether natural or artificial) is so low, exposure can commence as soon as administration begins (i.e. the administration time may effectively be zero). Thus, in a preferred aspect of the invention, photoactivation by sunlight may be effected immediately following administration of the photosensitiser. This is a particularly preferred form of treatment for skin disorders, e.g. in the treatment of acne. Moreover, it may also not be necessary to remove excess photosensitiser prior to photoactivation using sunlight therefore administration and photoactivation can be carried out at the same time. Indeed, it may in many cases be beneficial to retain excess photosensitiser at the site of administration such that administration essentially continues during photosensitisation. Since the intensity of natural sunlight may vary during the illumination period, if necessary, the light dose received by a subject from sunlight can easily be monitored by way of a portable photometer. Such photometers are commercially available from International Light Technologies. These monitor the total light dose and give a signal to the patient when the desired light dose has been reached.

The desired period of exposure to sunlight following administration of the photosensitiser will depend on various factors such as the nature of the composition, the condition to be treated, the form of administration, etc. but may readily be determined by those skilled in the art. It has, however, been found that the pain associated with PDT is less during the first 3 hours or so of exposure to sunlight and that this is sufficient for the desired therapeutic effects to be achieved. In a preferred aspect of the invention the period of exposure to sunlight may therefore be in the range of from 2 to 4 hours, e.g. about 3 hours.

In particularly preferred uses and methods of the invention, side effects of PDT are prevented or reduced by use of (i) as hereinbefore defined in combination with at least one of (ii), (iii) and (iv). Prevention or reduction of side effects by use of (i) in combination with (ii) or (iii), especially (ii), is particularly preferred.

In other particularly preferred uses and methods of the invention, side effects of PDT are prevented or reduced by use of (ii) as hereinbefore defined in combination with at least one of (iii) and (iv). Prevention or reduction of side effects by use of (ii) in combination with (iv) is particularly preferred. In these uses and methods, the photosensitiser is preferably administered for 15 to 45 minutes (e.g. for 30 minutes) prior to photoactivation. Preferably excess photosensitiser is not removed prior to photoactivation so administration may continue during the activation.

In further particularly preferred uses and methods of the invention, side effects of PDT are prevented or reduced by use of at least (i), (ii) and (iii) or (i), (ii) and (iv), e.g. (i), (ii) and (iii).

In yet further preferred embodiments of the invention, side-effects of PDT are prevented or reduced by use of (iii) in combination with (i) and/or (ii), e.g. by use of (iii) and (i); (iii) and (ii); or (iii) and (i) and (ii).

In other yet further preferred embodiments of the invention, side-effects of PDT are prevented or reduced by use of (iv) in combination with (i) and/or (ii), e.g. by use of (iv) and (i); (iv) and (ii); or (iv) and (i) and (ii).

In the methods and uses of the present invention, multiple treatments may be given, e.g. daily, weekly or monthly treatment. Preferably no more than two treatments are required, e.g. for PDT of acne.

The methods and uses of the invention may be used to treat any disease known to be treatable by PDT. Examples of diseases which may be treated include any malignant, pre-malignant and non-malignant abnormalities or disorders responsive to photochemotherapy e.g. cancers (e.g. basal cell carcinoma (bcc), tumours, squamous cell carcinoma (scc), Bowen's disease), skin disorders (e.g. psoriasis, actinic keratoses and acne) and infections (e.g. bacterial, viral or fungal infections, for example Herpes virus infections). The invention is particularly suited to the treatment of diseases, disorders or abnormalities where discrete lesions are formed to which the compositions may be directly applied (lesions is used here in a broad sense to include tumours and the like).

In some embodiments the uses and methods of the present invention are particularly suited to the treatment of diseases other than acne.

The internal and external body surfaces which may be treated according to the invention include the skin and all other epithelial and serosal surfaces, including for example mucosa, the linings of organs e.g. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue e.g. brain cavities following the excision of tumours such as gliomas.

Exemplary surfaces thus include: (1) skin and conjunctiva; (2) the lining of the mouth, pharynx, oesophagus, stomach, intestines and intestinal appendages, rectum, and anal canal; (3) the lining of the nasal passages, nasal sinuses, nasopharynx, trachea, bronchi, and bronchioles; (4) the lining of the ureters, urinary bladder, and urethra; (5) the lining of the vagina, uterine cervix, and uterus; (6) the parietal and visceral pleura; (7) the lining of the peritoneal and pelvic cavities, and the surface of the organs contained within those cavities; (8) the dura mater and meninges; (9) any tumors in solid tissues that can be made accessible to photoactivating light e.g. either directly, at time of surgery, or via an optical fibre inserted through a needle.

The uses and methods of the invention are particularly suited, however, to the PDT treatment of diseases of the face, scalp or neck, especially the face.

The uses and methods of the present invention are particularly suited to the treatment of acne. As used herein, the term "acne" includes both inflammatory and non-inflammatory diseases of the pilosebaceous unit. Primarily, however, the uses and methods herein described will be used for treating inflammatory types of acne where bacterial invasion of the pilosebaceous unit or follicles has occurred. The compounds described herein are preferably used for the treatment or prevention (preferably for the treatment) of acne associated with *Propionibacterium* bacteria (e.g. *P. acnes, P. granulosum* and *P. avidum*), especially *Propionibacterium acnes*.

Acne is categorised into different forms depending, for example, on the nature, severity and/or location of the black-heads, whiteheads, papules, pustules and/or cysts. Representative types of acne which may be treated according to the invention include acne vulgaris, acne rosacea, acne conglobate, acne papulosa and premenstrual acne, preferably acne vulgaris which is a chronic inflammatory disease of the pilosebaceous apparatus. Acne may occur on the back, chest, upper arms and/or face; the compounds described herein may be used for treating any of these areas of the body, especially the face.

The uses and methods of the present invention are also particularly suited to the treatment of cancers. Representative examples of cancers that may be treated include bcc, tumors, scc and Bowen's disease.

The invention will now be described in more detail by way of the following non-limiting Examples.

EXAMPLES

Example 1

A clinical Phase II study involving 23 males and 20 females (age 18 years or more) with facial acne vulgaris (papulo-pustular acne and at least 15 inflammatory, acne lesions on at least one side of the face) has been performed.

This study assessed porphyrin levels, safety and efficacy of PDT performed after application of three different concentrations of methylaminolevulinate (MAL) in a cream base. It further assessed the effect of different time intervals between MAL application and light exposure.

Patients were randomized to receive either MAL cream on the face at a concentration of 160 mg/g (16% wt), 80 mg/g (8% wt) or 40 mg/g (4% wt). Patients had skin biopsies taken on one half of the face (each patient had a total of two biopsies taken) and the other half of the face was exposed to red light (37 J/cm$^2$ using Photocure's Aktilite 128 LED light source) as indicated in the table below.

| Concentration of MAL in cream | Half of face Skin biopsies taken* (hrs) | Other half of face Illumination performed* (hrs) |
|---|---|---|
| 160 mg/g# | 0, 3 | 3 |
| 80 mg/g | 0, 0.5, 1, 1.5 | 0.5, 1, 1.5 |
| 40 mg/g | 0, 1, 1.5 | 1, 1.5 |

*Cream applied at 0 hrs.
Standard PDT treatment

Acne lesion counts (inflammatory and non inflammatory lesions for the half face exposed to red light) was performed at 0 hours as well as at day 14 and day 84 visits by a blinded evaluator. A Global Acne Severity Assessment was also performed at day 0, day 14 and day 84.

In vivo fluorescence spectroscopy was performed at 0 hours and immediately after red light exposure to measure porphyrin photobleaching after illumination. Sebum excretion rates were measured 7 days before day 0, at day 14 and day 84.

Safety was evaluated by medical questionnaire and adverse events reporting.

This study showed a significant difference between treatment groups in porphyrins levels after MAL application as measured with in vivo fluorescence spectroscopy. Porphrin levels were highest in facial skin of acne patients treated with MAL at 160 mg/g for 3 hours and 80 mg/g for 1.5 hours. These elevated levels went back to baseline levels after red light exposure.

Mean porphyrin levels were highest in sebaceous glands from biopsies taken 3 hours after application of 160 mg/g but there was no significant difference between treatment groups in mean porphyrin levels in sebaceous glands.

Surprisingly there was no difference between MAL-PDT treatment groups in inflammatory or non-inflammatory lesions at either day 14 or day 84. However a reduction from the start of the study in inflammatory lesions (between 23% to 44% at Day 84) was noted for all groups on the MAL-PDT treated side. There was no difference between treatment groups in Global acne severity scores or sebum excretion rates at day 14 and day 84 thus showing that all treatment regimes were equally efficient.

Mean pain during light exposure was evaluated by patients on a visual analog scale where 0=no pain, 50=moderate pain and 100=worst possible pain. The results are shown in the Table below.

| Pain during light exposure | | | |
|---|---|---|---|
| Treatment | n | Mean | Std Dev |
| 1 h after MAL (40 mg/g) | 8 | 2 | 4 |
| 1.5 h after MAL (40 mg/g) | 8 | 19 | 19 |
| 0.5 h after MAL (80 mg/g) | 6 | 1 | 1 |
| 1 h after MAL (80 mg/g) | 8 | 9 | 16 |
| 1.5 h after MAL (80 mg/g) | 6 | 32 | 32 |
| 3 h after MAL (160 mg/g)# | 7 | 64 | 13 |

Standard PDT treatment

There was a statistically significant difference between groups in mean pain during light exposure (p=0.0006). Pairwise comparison between the 160 mg/g 3 h group and all other groups showed a higher mean pain during light exposure for the 160 mg/g group except for the comparison with the 80 mg/g 1.5 h group which was at the limit of significance (p=0.06). In fact, for a few patients in these two groups the pain was so strong that the light delivery had to be interrupted (2 patients) or ended (2 patients). This shows that pain is related to exposure time and MAL concentration.

The duration of post-PDT erythema is presented in the Table below. This information was derived from the journal kept by patients. The longest mean duration of erythema (14 days) was seen in patients treated with 160 mg/g for 3 hours and the shortest (0.5 days) was seen in patients treated with 40 mg/g for 1 hour. There is a significant difference among the 6 groups in the duration of post PDT erythema (p=0.03).

| Duration of post PDT erythema (in days) | | | |
|---|---|---|---|
| Treatment | n | Mean | Std Dev |
| 1 h after MAL (40 mg/g) | 4 | 4 | 6.7 |
| 1.5 h after MAL (40 mg/g) | 6 | 1.8 | 1.3 |
| 0.5 h after MAL (80 mg/g) | 0 | — | — |
| 1 h after MAL (80 mg/g) | 5 | 2.1 | 2.7 |
| 1.5 h after MAL (80 mg/g) | 3 | 3.7 | 0.6 |
| 3 h after MAL (160 mg/g)# | 7 | 11.9 | 11.7 |

Standard PDT treatment

This shows that post-PDT erythema is related to exposure time and MAL concentration.

The study shows that there was no significant difference in the therapeutic effect between groups, but there was a significant difference between groups for the duration of post-PDT erythema, local tolerance to PDT and pain during light exposure which was longest, lowest and highest respectively in the 160 mg/g 3 h group.

Example 2

A study was performed to evaluate the effect of reducing the fluence rate during illumination.

34 patients with moderate to severe facial acne vulgaris were treated full-face with Metvix® (160 mg/g) applied for three hours under occlusion. The cream was removed, and the treatment area was illuminated with a total light dose of 37 J/cm$^2$ using the Aktilite® 128 lamp (Photocure ASA, Norway). This lamp consists of 128 light emitting diodes (LEDs) and has a peak wavelength of 634±3 nm.

15 patients had one PDT treatment with no curettage prior to Metvix® application and using a fluence rate of 34 mW/cm$^2$. The remaining 19 acne patients were supposed to have 2 PDT treatments and were illuminated with a fluence rate of 68 mW/cm$^2$ and curettaged before the first treatment. 12 of these patients had 2 PDT treatments and 7 patients only one treatment.

The treatment effect was evaluated as reduction in number of inflammatory acne lesions from baseline to 12-week control. Pain during illumination was assessed using a numerical scale ranging from 0 to 10 in which 0 is no pain and 10 is worst imaginable pain.

The results are summarised in the table below:

| FLUENCE RATE | Number of patients | Reduction inflammatory acne lesions Median percentage | P value |
|---|---|---|---|
| 68.5 mW/cm$^2$ | 19 | 70% | 0.92 |
| 34 mW/cm$^2$ | 15 | 59% | |

It is evident from the table that there was no significant difference between the two groups with respect to treatment effect.

| FLUENCE RATE | Number of treatment sessions | Maximal Pain Median (IQR) | P value | *Corrected P value |
|---|---|---|---|---|
| 68.5 mW/cm² | 31 | 8 (6, 10) | 0.018 | 0.009 |
| 34 mW/cm² | 15 | 6 (5, 7) | | |

*By correcting the pain scores for differences in porphyrin fluorescence (measured by quantitative fluorescence imaging) in the treatment area, we take into account differences in curettage and treatment number between the two treatment groups.

Example 3

A study was performed to demonstrate that illumination with sunlight is as effective as if a PDT lamp was used.

Patients with actinic keratosis (23 men and 6 women) median age 80 years (63-93 years) were included in this study.

A gentle curettage was performed followed by application of Metvix® cream (160 mg/g). The treated area was then occluded. After 30 minutes the occlusion was removed on half the treatment area, which was then exposed to sunlight for 2.5 hours.

The occlusion was then removed on other half followed by illumination using the Aktilite® 128 lamp (Photocure ASA, Norway)—for details see Example 2. Photodynamic treatment was performed with a total light dose of 37 Joules/cm² and a fluence rate of 68.5 mW/cm².

| | Sunlight exposure | |
|---|---|---|
| LUX* | No. of patients | Mean LUX |
| >80,000 | 14 | 92,362 |
| 50,000-80,000 | 9 | 68,277 |
| <50,000 | 6 | 38,296 |

*1 LUX = 1 lumen/m²

The treatment effect was scored by lesion counting before treatment and 12 weeks after the PDT treatment:

| Treatment effect | | | |
|---|---|---|---|
| | SUNLIGHT Median (range) | RED LIGHT Median (range) | p value* |
| Number of lesions before treatment | 9 (2-27) | 9 (1-32) | 0.76 |
| Number of lesions at 12 week follow up | 2 (0-8) | 3 (0-9) | 0.35 |
| Absolute decrease (number of lesions) | 7 (1-22) | 6 (0-27) | 0.58 |
| Lesions with complete response (percent) | 81 (43-100) | 75 (0-100) | 0.19 |

*Sunlight group vs. red light group

Pain was scored using a numerical scale ranging from 0 to 10 in which 0 is no pain and 10 is worst imaginable pain.

| | Pain | |
|---|---|---|
| Light exposure | Maximal pain Median (range) | p value |
| Sunlight | 2 (0-6) | <0.0001 |
| Red light | 7 (2-10) | |

It is evident from the table that there was no significant difference between the two illumination groups with respect to the absolute decrease in number of lesions or in the percentage of lesions with a complete response. It can therefore be concluded that exposure of continuously formed protoporphyrin to sunlight during 2.5 hours treatment with Metvix® is as efficient as illumination with red light after 3 hours of incubation with Metvix®.

Pain during light exposure was significantly lower in the sunlight group. There was no significant correlation between intensity of the sunlight exposure and the reduction in lesions in the area treated with Metvix® and sunlight (p=0.66). Neither was there any significant correlation between intensity of the sunlight exposure and pain during exposure (p=0.1036).

The invention claimed is:

1. A method of treating pre-malignant and malignant abnormalities and disorders of at least one of a lining of the vagina, cervix or uterus in an animal by photodynamic therapy (PDT), wherein said PDT comprises:
    (a) administering to said animal a composition comprising an ester of 5-aminolevulinic acid (5-ALA) or a pharmaceutically acceptable salt thereof, as a photosensitiser; and
    (b) photoactivating said photosensitiser,
and wherein side-effects of said PDT are prevented or reduced by use of (i) in combination with (ii):
    (i) said composition comprises said photosensitiser in a concentration of less than 10% wt,
    (ii) said photoactivation is carried out with a light source comprising a light emitting diode and having a fluence rate of less than 50 mW/cm².

2. The method of claim 1, wherein said PDT has substantially the same therapeutic effect as the corresponding standard PDT treatment.

3. The method of claim 1, wherein said photosensitiser is a compound of general formula I:

$$R^2{}_2N\text{—}CH_2COCH_2\text{—}CH_2CO\text{—}OR^1 \tag{I}$$

(wherein $R^1$ represents a substituted or unsubstituted, straight-chained, branched or cyclic alkyl group; and each $R^2$ independently represents a hydrogen atom) or a pharmaceutically acceptable salt thereof.

4. The method of claim 3, wherein in formula I, $R^1$ represents an unsubstituted alkyl group or an alkyl group substituted by an aryl group.

5. The method of claim 1, wherein said composition further comprises a second photosensitiser.

6. The method of claim 1, wherein the photosensitizer is hexyl ALA ester (HAL) or a pharmaceutically acceptable salt thereof.

7. The method of claim 6, wherein the photosensitizer is the hydrochloric acid salt of hexyl ALA ester (HAL).

8. The method of claim 1, wherein the abnormality or disorder is pre-malignant.

9. The method of claim 8, wherein the abnormality or disorder is a pre-malignant lesion of the cervix.

10. The method of claim 9, wherein the abnormality or disorder is a viral infection.

11. The method of claim 9, wherein the photosensitizer is hexyl ALA ester (HAL) or a pharmaceutically acceptable salt thereof.

12. The method of claim 11, wherein the photosensitizer is the hydrochloric acid salt of hexyl ALA ester (HAL).

13. The method of claim 12, wherein the photosensitizer is present in the composition at a concentration of 0.05 percent to 8 percent by weight.

14. The method of claim 13, wherein the photosensitizer is present in the composition at a concentration of 2 percent to 8 percent by weight.

15. The method of claim 1, wherein the fluence rate is 5 to 40 mW/cm$^2$.

16. The method of claim 1, wherein the animal is a human and the lining is the lining of the cervix.

* * * * *